(12) United States Patent
Rosengren et al.

(10) Patent No.: US 9,597,307 B2
(45) Date of Patent: Mar. 21, 2017

(54) SULFORAPHANE FOR TREATING OR REDUCING INSULIN RESISTANCE OF THE LIVER

(71) Applicants: Anders Rosengren, Malmö (SE); Annika Axelsson, Lund (SE)

(72) Inventors: Anders Rosengren, Malmö (SE); Annika Axelsson, Lund (SE)

( * ) Notice: Subject to any disclaimer, the term of this patent is extended or adjusted under 35 U.S.C. 154(b) by 0 days.

(21) Appl. No.: 14/443,907

(22) PCT Filed: Nov. 19, 2013

(86) PCT No.: PCT/EP2013/074201
§ 371 (c)(1),
(2) Date: May 19, 2015

(87) PCT Pub. No.: WO2014/076312
PCT Pub. Date: May 22, 2014

(65) Prior Publication Data
US 2015/0290164 A1    Oct. 15, 2015

(30) Foreign Application Priority Data
Nov. 19, 2012  (SE) ...................................... 1251306

(51) Int. Cl.
*A61K 31/26*       (2006.01)
*A61K 36/31*       (2006.01)

(52) U.S. Cl.
CPC .............. *A61K 31/26* (2013.01); *A61K 36/31* (2013.01)

(58) Field of Classification Search
CPC ................................ A61K 31/26; A61K 36/31
See application file for complete search history.

(56) References Cited

U.S. PATENT DOCUMENTS 8,017,147 B2 * 9/2011 Mazed ................... A61K 36/02
424/450

OTHER PUBLICATIONS

Yang et al., Zhongguo Zuzhi Gongcheng Yanjiu (Chinese Journal of Tissue Engineering Research) (2012), 16(2), 320-324.*
Bahadoran et al. International Journal of Food Sciences and Nutrition, 63(7), (2012), p. 767-771, published online Apr. 26, 2012.*
Solowiej et al, (2006), Transplantation Proceedings, V.38, p. 282-283.*
Yang et al., Zhongguo Zuzhi Gongcheng Yanjiu (Chinese Journal of Tissue Engineering Research) (2012), 16(2), 320-324 (English translation.*
Abdul-Ghani Muhammad A et al: "Muscle and liver insulin resistance indexes derived from the oral glucose tolerance test.", Diabetes Care Jan. 2007, vol. 30, No. 1, Jan. 2007, pp. 89-94.
Bahadoran Zahra et al: "Effect of Broccoli Sprouts on Insulin Resistance in Type 2 Diabetic Patients: A Randomized Double-Blind Clinical Trial.", International Journal of Food Sciences and Nutrition, vol. 63, No. 7, Nov. 2012, pp. 767-771.
Choukem S P et al: "How to measure hepatic insulin resistance?", Diabetes & Metabolism, Paris, Amsterdam, NL, vol. 34, No. 6, Dec. 2008, pp. 664-673.
JP2008247805A—Abstract Database WPI,Thomson Scientific, London, GB; AN 2008-M25230, (Univ Iwate) Oct. 16, 2008.
JP2005047822A Abstract—Database WPI, Thomson Scientific, London, GB; AN 2005-176026 (Kin Sirusi Masabi KK) Feb. 24, 2005.
De Souza Carolina Guerini et al: "Metabolic effects of sulforaphane oral treatment in streptozotocin-diabetic rats.", Journal of Medicinal Food Sep. 2012, vol. 15, No. 9, Sep. 2012, pp. 795-801.
International Search Report and Written Opinion for PCT/EP2013/074201, dated Feb. 19, 2014, 6 pages.
Meshkani R et al: "Hepatic insulin resistance, metabolic syndrome and cardiovascular disease", Clinical Biochemistry, Elsevier Inc, US, CA, vol. 42, No. 13-14, Sep. 2009, pp. 1331-1346.
Xu, Jialin, et al., Enhanced Nrf2 Acticity Worsens Insulin Resistance, Impairs Lipid Accumulation in Adipose Tissue, and Increases Hepatic Steatosis in Leptin-Deficient Mice, Diabetese, vol. 61, pp. 3208-3218, Dec. 2012.

* cited by examiner

*Primary Examiner* — Yong Chu
(74) *Attorney, Agent, or Firm* — Honigman Miller Schwartz and Cohn LLP; Noel E. Day; Anna M. Budde

(57) ABSTRACT

The present invention provides sulforaphane, or a plant extract comprising sulforaphane, for treating or reducing insulin resistance of the liver. Especially, there is provided sulforaphane, or a plant extract comprising sulforaphane, for treating or reducing insulin resistance of the liver, wherein, in the subject to be treated, the insulin resistance index of the liver is higher than the insulin resistance of other metabolic tissue.

14 Claims, 2 Drawing Sheets

SULFORAPHANE FOR TREATING OR REDUCING INSULIN RESISTANCE OF THE LIVER

This application is a 35 USC §371 United States National Phase Application of, and claims priority to, PCT International Application No. PCT/EP2013/074201 filed Nov. 19, 2013, which claims the benefit to Swedish Application Serial No. 1251306-5 tiled Nov. 19, 2012. The entire contents of the aforementioned applications are incorporated herein, by reference in their entireties.

FIELD OF THE INVENTION

The present invention relates to treatment of insulin resistance of the liver.

BACKGROUND OF THE INVENTION

Diabetes mellitus type 2 is a metabolic disorder that is characterized by high blood glucose in the context of insulin resistance (IR) and relative insulin deficiency. Type 2 diabetes makes up about 90% of cases of diabetes and is predominantly thought to be caused by obesity, which results from a sustained imbalance between energy intake and expenditure. It is estimated that more than one-third of the U.S. adult population over 20 years of age had the insulin resistance syndrome in the year 2000, and therefore are at high risk for the development of type 2 diabetes and cardiovascular disease (Ford ES. "Prevalence of the metabolic syndrome defined by the International Diabetes Federation among adults in the U.S." Diabetes Care 28:2745-2749, 2005).

Type 2 diabetes is initially treated by and dietary modifications and increased exercise. If blood glucose levels are not lowered to an adequately level, patients are usually treated with a number of standard medications such as metformin, an oral antidiabetic drug in the biguanide class. Metformin needs to be regulated to individual patient requirements and in rare cases, metformin can cause lactic acidosis. All patients do not respond to metformin and it is not given to patients with renal insufficiency. For patients who do not respond to metformin, thiazolidinediones are given to improve glucose uptake and blood lipid profile. However, thiazolidinedione treatment has been connected to increased mortality in large prospective studies, why thiazolidinediones are now prescribed with great care.

Many tissues, including the liver, skeletal muscle, and adipocytes, manifest resistance to insulin (Groop L C et.al. "Role of free fatty acids and insulin in determining free fatty acid and lipid oxidation in man". J Clin Invest 87:83-89, 1991). Although in many individuals the insulin resistance develops simultaneously in multiple organs, the severity of insulin resistance may differ among the various tissues. Present medications don't target a specific tissue, but insulin resistance in general. Subjects suffering from insulin resistance, wherein the insulin resistance is more prominent in on type of tissue would benefit from treatment targeting this tissue. While present medications don't target a specific tissue, present methods allows for quantification of organs which are resistant to insulin, as well as quantification of the magnitude of insulin resistance in each organ.

Glucose metabolism in controlled by a complex interplay of metabolically active tissues. Glucose is taken up by muscles in a process which is mediated by insulin. When muscle tissue is insulin-resistant, glucose uptake decreases, leading to higher blood glucose. The fat tissue stores lipids from the blood, in a process that is also regulated by insulin. Finally, the liver plays an important role in the regulation of blood glucose by regulating glucose production. Insulin inhibits glucose production from the liver. Hence, if the liver is insulin-resistant, glucose production will not be appropriately inhibited after a meal, contributing to high blood glucose.

It has been shown that some patients with type 2 diabetes have primarily perturbations in muscle insulin sensitivity, while hepatic insulin resistance is predominant in other patients (Shulman, G. I. (2000). "Cellular mechanisms of insulin resistance". J. Clin. Invest. 106, 171-176.; Jornayvaz and Shulman, "Diacylglycerol Activation of Protein Kinase Ce and Hepatic Insulin Resistance", Cell 2012 15: 574-; Björnholm and Zierath. "Insulin signal transduction in human skeletal muscle: identifying the defects in Type II diabetes". Biochemical Society Transactions (2005) Volume 33, part 2).

As only some patients with type 2 diabetes suffer from predominant hepatic insulin resistance, a medication targeting insulin resistance in the liver would be of specific interest.

Thus, there is a need for a new treatment for treating or reducing insulin resistance of the liver. Preferably, such treatment should have limited side effects. Also, such treatment should preferably be safely used in combination with other drugs that are in common use in insulin resistant patients, such as antidiabetic drugs, antihypertensive drugs, cholesterol-reducing agents, and insulin.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing sulforaphane, or a plant extract comprising sulforaphane, for use in treating or reducing insulin resistance of the liver and/or for use in improving hepatic insulin sensitivity. Especially, there is provided sulforaphane, or a plant extract comprising sulforaphane, for treating or reducing insulin resistance of the liver and/or for improving hepatic insulin sensitivity, wherein, in the subject to be treated, the insulin resistance index of the liver is higher than the insulin resistance of other metabolic tissue.

Sulforaphane has been shown to possess specific effects on insulin resistance of the liver. Its effect on insulin resistance in other organs and tissue is much less pronounced, if active at all. These previously unknown properties provide for use of sulforaphane in subjects suffering from insulin resistance of the liver and to much a less extent in other tissue.

Sulforaphane is a compound from the isothiocyanate group of organosulfur compounds. It is known to exhibit antimicrobial and anticancer properties from experimental trials. It can be isolated from cruciferous vegetables, such as broccoli, Brussels sprouts or cabbages. Sulforaphane is in numerous clinical trials (Clinical Trials.gov, a service of the U.S. National Institutes of Health). Studies have shown sulforaphane to have low toxicity even at high doses, and no serious adverse events have been reported from ongoing studies for other indications.

Sulforaphane, or a plant extract comprising sulforaphane, may not only be used in treating or reducing insulin resistance of the liver and/or in improving hepatic insulin sensitivity. It may also, according to an aspect of the invention, be used in the manufacture of a medicament for use in the treatment and/or in reducing insulin resistance of the liver and/or for use in improving hepatic insulin sensitivity.

Further, sulforaphane, or a plant extract comprising sulforaphane may be used in a method of preventing and/or treating insulin resistance of the liver and/or in a method of improving hepatic insulin sensitivity. Such a method comprises administering to a mammal, including man, in need of such prevention and/or treatment, a therapeutically effective amount of sulforaphane, or a plant extract comprising sulforaphane.

Similarly, as sulforaphane is effective in reducing insulin resistance of the liver, one embodiment of the invention relates to use of sulforaphane, or a plant extract comprising sulforaphane, for the use in the treatment and/or improvement of glucose tolerance.

When used to prevent, treat and/or reduce insulin resistance of the liver, the daily administered dose of sulforaphane typically is from 10 to 1000 µmole, such as 50 to 500 µmole, e.g. 100 to 200 µmole, sulforaphane. Sulforaphane, or a plant extract comprising sulforaphane, may be administrated in various ways. Preferred routes include injection, e.g. intra peritoneal injection, and oral administration. In terms of body weight, the daily administered dose of sulforaphane administered to a subject to be treated may be from 1 to 100 mg/kg of the subjects body weight, such as 5 to 50 mg/kg of the subjects body weight, e.g. about 10 mg/kg of the subjects body weight.

As already described, when sulforaphane, or a plant extract comprising sulforaphane, is used to prevent, treat and/or reduce insulin resistance of the liver it is preferred if the insulin resistance index of the liver subject to be treated is higher than the insulin resistance of other metabolic tissue. Especially, it is preferred if the insulin resistance index of the liver in the subject to be treated is higher than the insulin resistance index of body fat or muscles. While sulforaphane, or a plant extract comprising sulforaphane, is effective in reducing the insulin resistance of the liver, it has no, or very limited activity, on other metabolic tissue. Thus, sulforaphane, or a plant extract comprising sulforaphane, should only be used to treat insulin resistance of the liver. Subjects only suffering form insulin resistance in other metabolic tissue than the liver may not benefit from treatment with sulforaphane and may even be adversely affected. Therefore it is important to only target subjects suffering form insulin resistance in the liver.

According to an embodiment, sulforaphane, or a plant extract comprising sulforaphane, is used to prevent, treat and/or reduce insulin resistance of the liver in subjects, whose insulin resistance of other metabolic tissue than the liver not is increased.

According to an embodiment, sulforaphane, or a plant extract comprising sulforaphane, is used to improve the insulin sensitive index of the liver in subjects, whose insulin sensitive index of the liver is lower than the insulin sensitive of other metabolic tissue. Especially, sulforaphane, or a plant extract comprising sulforaphane, may be used to improve the insulin sensitive index of the liver in subjects, whose insulin sensitive index of the liver is lower than the insulin sensitive index of body fat or muscles. Further, sulforaphane, or a plant extract comprising sulforaphane, is, according to an embodiment, used to improve the insulin sensitive index of the liver in subjects, whose insulin sensitive of other metabolic tissue than the liver not is decreased.

Sulforaphane may be used in isolated form, having a purity of at least 99 wt %. As readily understood by the skilled person, isolated sulforaphane is typically formulated into a pharmaceutical composition with pharmaceutical acceptable excipient(s). Such a pharmaceutical composition will typically comprise less than 99 wt % sulforaphane. The skilled person is familiar with the practice of formulating sulforaphane into pharmaceutical composition comprising sulforaphane. Examples of such formulations are known in the art.

Further, sulforaphane may be used in form of a plant extract comprising sulforaphane. Plant extracts may be obtained from Brussels sprouts, cabbage, cauliflower, bok choy, kale, collards, broccoli sprouts, Chinese broccoli, broccoli raab, kohlrabi, mustard, turnip, radish, arugula, or watercress.

According to an alternative embodiment, sulforaphane is replaced by a compound according to formula I

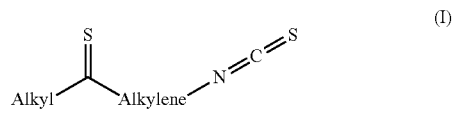

wherein alkyl denotes a saturated, straight or branched alkyl group having 1 to 10, such as 1 to 5, carbon atoms; and alkylene denotes a saturated, straight of branched alkylene group having 1 to 10, such as 3 to 8, carbon atoms and linking the thiocarbonyl and isothiocyanate group;

with the proviso that the alkyl not is methyl when the alkylene is n-butylene (—CH$_2$)$_4$—).

BRIEF DESCRIPTION OF THE DRAWINGS

These and other aspects, features and advantages of which the invention is capable of will be apparent and elucidated from the following description of embodiments of the present invention, reference being made to the accompanying drawings, in which FIG. 1 displays tolerance levels of an oral glucose challenge to rats treated with sulforaphane compared to vehicle-treated rats (control).

DETAILED SUMMARY OF PREFERRED EMBODIMENTS

Figure 1:
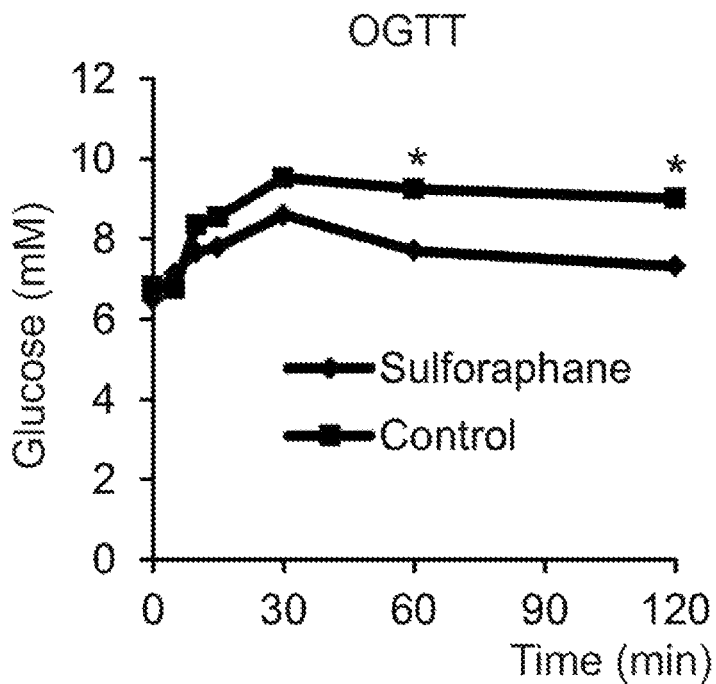

Sulforaphane is the first compound shown to have specific effects on insulin resistance in the liver. This is based on extensive in vivo data from animals treated with diet with high fructose content, which is a classic way to induce insulin resistance without any genetic modifications. With oral glucose tolerance test, the inventors have found that glucose tolerance is improved significantly after two weeks of daily injections with sulforaphane (10 mg/kg). The inventors have also made treatment intraperitoneal pyruvate tolerance tests that specifically reflect insulin sensitivity in the liver, with significant positive effect of sulforaphane. At the insulin tolerance test which measures the insulin sensitivity in fat and muscle, no effects have been seen from sulforaphane treatment. The experiments have been repeated several times, also in animals on high-fat diet, with positive results.

Sulforaphane is already being tested clinically for other indications (cancer and immune diseases) with very low toxicity even at high doses.

This makes sulforaphane the first potential drug against insulin resistance in the liver. A more specific therapy based on sulforaphane could thus provide better disease control and fewer side effects than the existing general Diabetes mellitus type 2 and insulin resistance treatments could therefore be provided.

It has been suggested that broccoli sprouts may improve insulin resistance in type 2 diabetic patients (cf. Zahra Bahadoran et.al., "*Effect of broccoli sprouts on insulin resistance in type 2 diabetic patients: a randomized double-blind clinical trial*" International Journal of Food Sciences and Nutrition, November 2012; 63(7): 767-771). It is suggested that strengthening the antioxidant system may be important in preventing the activation of these pathways, and that broccoli sprouts are rich sources of bioactive components including isothiocyanates, glucosinolates, flavonoids, phenols, carotenoids, antioxidant vitamins, selenium, and expecially sulphoraphane as a potent inducer of antioxidant enzymes. A double-blind and placebo controlled study of Type 2 diabetic patients reported no ill effects of the broccoli sprouts powder (BSP) trials. Fasting plasma glucose and serum insulin concentrations were measured and a general improvement was seen for the BSP group. However, no specific effects of sulforaphane on insulin resistance in the liver was assessed or expected. Thus, from this publication, the skilled person would have no reason to believe that sulforaphane would by any different from other drugs targeting insulin resistance in general.

Without further elaboration, it is believed that one skilled in the art can, using the preceding description, utilize the present invention to its fullest extent. The preferred specific embodiments described herein are, therefore, to be construed as merely illustrative and not limitative of the remainder of the description in any way whatsoever. Further, although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous.

In addition, singular references do not exclude a plurality. The terms "a", "an", "first", "second" etc do neither preclude a plurality.

Experimental

The following examples are mere examples and should by no mean be interpreted to limit the scope of the invention. Rather, the invention is limited only by the accompanying claims.

Study the Mechanisms and Clinical Effect of the Anti-Diabetic Drug Candidate Sulforaphane, Identified by Network Analysis An attractive strategy for expanding the therapeutic options is drug repositioning, which implies finding new indications either for approved drugs or for the thousands of compounds that have passed toxicology tests but not yet reached clinical use. One potential benefit with repositioning is that the road to clinical implementation can be considerably shorter compared with de novo drug development. In a first attempt to use gene network analyses for drug repositioning, a panel of 50 genes that are perturbed in the liver in T2D ('T2D signature') were identified. The genes were selected using differential expression analysis, causality tests, and a Bayesian network algorithm to identify genes that regulate the expression of several other disease genes ('key regulators'). Further, a library of >2500 drug signatures derived from the Connectivity Map and from public microarray data (http://www.ncbi.nlm.nih.gov/geo/) that are of particular relevance for metabolic diseases were compiled. A drug signature represents genes for which the expression is significantly affected by a compound.

The drug signatures were matched with the T2D signature using Gene Set Enrichment Analysis to find drugs that could reverse aberrantly expressed disease genes (overexpressed T2D genes should be downregulated in the drug signature and vice versa). The highest ranked compound was sulforaphane, which is an isothiocyanate contained in green vegetables. Among the top-ranked compounds were also the known anti-diabetic drugs metformin and rosiglitazone. Sulforaphane is being studied clinically for cancer and immune disorders.

As the Gene set chosen were intended to be representative for the liver, it was envisaged that sulforaphane should be effective in reducing insulin resistance, which was confirmed in animal experiments. Further, this finding is supported in the art. It was however also surprisingly found that sulforaphane was selective for insulin resistance of the liver. Neither the Gene Set Enrichment Analysis nor the art, provided any guidance towards this finding. The finding is important as it provides for the use of sulforaphane for selective targeting insulin resistance of the liver Insulin Sensitivity and Insulin Resistance The insulin sensitivity index of the liver, other metabolic tissue and body fat or muscles can be quantified using the hyperinsulinemic-euglycemic clamp method in combined with radiolabeled glucose (DeFronzo R A etal. "Hepatic and peripheral insulin resistance: a common feature of type 2 (non-insulindependent) and type 1 (insulin-dependent) diabetes mellitus". Diabetologia 23: 313-319, 1982). It has also been shown that measurements of plasma glucose and insulin concentrations during the oral glucose tolerance test (OGTT) can be used to derive indexes that can selectively quantitate hepatic and muscle insulin resistance (Abdul-Ghani, A. M. et.al., "Muscle and Liver Insulin Resistance Indexes Derived From the Oral Glucose Tolerance Test". Diabetes Care, volume 30, number 1, January 2007).

The measurement of the hepatic insulin sensitivity is based on the following logic: in the postabsorptive state, the higher the rate of endogenous glucose production (EGP) and the higher the fasting plasma insulin (FPI) concentration, the greater Because 80-85% of EGP originates in the liver, basal EGP primarily reflects hepatic glucose production (HGP), and we use EGP and HGP interchangeably. The product of EGP and FPI, therefore, provides a measure of hepatic insulin resistance under postabsorptive conditions.

Following the glucose load, the rise in plasma glucose concentration stimulates insulin secretion from the β-cells, and the combination of hyperglycemia and hyperinsulinemia suppress EGP. In subjects with normal hepatic insulin sensitivity, the rise in plasma glucose and insulin concentrations is sufficient to suppress EGP and ameliorate the rise in plasma glucose concentration. On the other hand, in hepatic insulin-resistant individuals, an even greater rise in plasma glucose and insulin concentrations causes only a small to moderate suppression of EGP, and this result in a greater increase in plasma glucose concentration during the early phase (0-30 min) of the OGTT. It follows that the magnitude of the rise in plasma glucose and insulin concentrations immediately (0-30 min) following the glucose load is proportional to the magnitude of hepatic insulin resistance. We previously have shown that during the initial 20 min of insulin infusion, muscle glucose uptake is minimally increased, whereas HGP is markedly inhibited in NGT individuals. The rise in plasma glucose and insulin concentrations can be quantitated by the incremental area under the curve (AUC) for plasma glucose and insulin. Therefore, the total AUC during the OGTT reflects the combination of the fasting plasma glucose/insulin concentrations and the rise in plasma glucose/insulin concentrations, and the product of glucose AUC and insulin AUC provides an index of hepatic insulin resistance. Because the suppression of EGP during the OGTT reaches its nadir 45-60 min following ingestion of a glucose load, we calculated the product of the glucose and insulin AUCs during the first 30 min during the OGTT as the hepatic insulin sensitivity index. We compared this index against hepatic insulin sensitivity directly measured with EGP * FPI. The rise in plasma glucose concentration during the OGTT stimulates glucose disposal into peripheral tissues, primarily skeletal muscle. Because there is no significant change in the rate of EGP production during the 60- to 120-min time period of the OGTT, the decline in plasma glucose concentration after 60 min primarily reflects glucose uptake by peripheral tissues, skeletal muscle. Therefore, the decline from the peak plasma glucose concentration during the OGTT is determined by the combination of two factors: 1) skeletal muscle insulin resistance and 2) plasma insulin concentration. The greater the muscle insulin resistance and the lower the plasma insulin concentration, the slower is the decline in plasma glucose concentration. Thus, skeletal muscle insulin sensitivity can be calculated as the rate of decline in plasma glucose concentration divided by plasma insulin concentration, as follows. Muscle insulin sensitivity index=dG/dt/mean plasma insulin concentration (I), where dG/dt is the rate of decline in plasma glucose concentration and is calculated as the slope of the least square fit to the decline in plasma glucose concentration from peak to nadir. It should be noted that in some cases plasma glucose concentration has rebounded after it reached its nadir. In such instances, the rebound glucose concentration was not included in the regression. It represents the mean plasma insulin concentration during the OGTT. During the last 30 min of the hyperinsulinemic-euglycemic clamp, HGP is suppressed by >85-90% in NGT and IGT subjects and glucose disposal mainly reflects insulin sensitivity of the skeletal muscle. Therefore, we validated the proposed skeletal muscle insulin sensitivity index during the OGTT against the rate of whole-body insulin-mediated glucose disposal measured with the euglycemic insulin clamp. All data are expressed as means ±SD.

According to an embodiment, sulforaphane, or a plant extract comprising sulforaphane, is used in treating or reducing insulin resistance of the liver and/or in improving hepatic insulin sensitivity in patients, such as patients with type 2 diabetes, who have more pronounced insulin resistance in the liver, as measured by the index in Abdul-Ghani, A. M. et.al., compared with the insulin resistance in muscles, as measured by the oral glucose insulin sensitivity index (OGIS), as described in (Mari et al. "A Model-Based Method for Assessing Insulin Sensitivity From the Oral Glucose Tolerance Test". Diabetes Care 24:539-548, 2001).

In Vivo Sulforaphane Treatment Glucose Tolerance Tests

For glucose tolerance tests, a high fructose diet was used to induce insulin resistance on a group of Wistar rats. Part of the group received a two week treatment period of daily intraperitoneal sulforaphane injections (10 mg/kg). During glucose tolerance tests, glucose was given to the animal and afterwards blood samples were collected at an interval to monitor the rate by which the glucose is cleared from the blood. Detailed test results are found in FIG. 1. Glucose tolerance between animals treated with sulforaphane and the vehicle-treated control group showed significant differences. Daily sulforaphane injections significantly improved glucose tolerance in rats with diet-induced diabetes. This general test also reflects the insulin resistance of the liver.

In Vivo Sulforaphane Treatment Intraperitoneal Pyruvate Tolerance Tests

Figure 2:
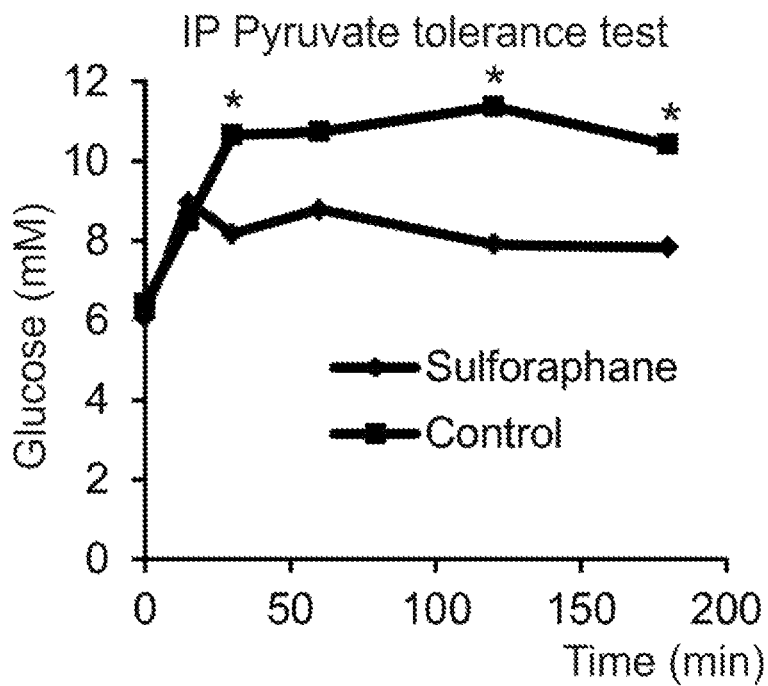
FIG. 2 displays tolerance levels of an intraperitoneal pyruvate challenge to rats treated with sulforaphane compared to vehicle-treated rats (control)

For intraperitoneal pyruvate tolerance tests, a high fructose diet was used to induce insulin resistance on a group of Wistar rats. Part of the group received a two week treatment period of daily sulforaphane injections (10 mg/kg). Intraperitoneal pyruvate tolerance tests are a procedure where pyruvate is converted to glucose in gluconeo-genesis. The test specifically reflects the insulin sensitivity of the liver. Sulforaphane treated animals showed significant differences from a vehicle-treated control group during intraperitoneal pyruvate tolerance tests, and detailed test results are found in FIG. 2.

In Vivo Sulforaphane Treatment Insulin Tolerance Tests

For Insulin tolerance tests (ITT), a high fructose diet was used to induce insulin resistance on a group of Wistar rats. Part of the group received a two week treatment period of daily sulforaphane injections (10 mg/kg). ITT is a procedure during which insulin is injected into a subject's vein to access pituitary function and adrenal function. The Insulin injections induce hypoglycemia, and as a part of a stress mechanism Adrenocorticotropic hormone (ACTH) and Growth Hormone (GH) are released to counteract hypoglycemia. ACTH causes Cortisol to be released from the adrenal cortex, which together with GH will oppose the action of insulin (Greenwood F. C. et.al. "The plasma sugar, free fatty acid, Cortisol, and growth hormone response to insulin. I. In control subjects". J Clin Invest (1965)45 (4): 429-). ITT primarily mirrors the insulin sensitivity in muscle tissue and fat. Animals treated with sulforaphane did not show significant differences from a vehicle-treated control group during ITT, thus the sulfophrane treatment did not affect the insulin sensitivity of the muscle tissue and fat. This experiment, thus clearly shows that the effects of sulfophrane on insulin sensitivity are selective for the liver.

Sulforaphane Treatment Fisher's Exact Tests

A high fructose diet was used to induce insulin resistance on a group of Wistar rats. Part of the group received a two week treatment period of daily sulforaphane injections (10 mg/kg). Interestingly, microarray analysis of liver extracted from these animals showed that a major fraction of the genes in the T2D signature was reversed in sulforaphane-treated rats ($p<0.0001$ using Fisher's exact test), indicating the anti-diabetic properties from sulforaphane treatment.

Sulforaphane Treatment Specifically Improves Hepatic Insulin Sensitivity

H-4-II-E cells were seeded 110,000/well in 24-well plates in their usual medium (EMEM from ATCC, no 30-2003 with addition of 10% FBS and penicillin/streptomycin) at day 0 and incubated with 0.25 mM palmitate-BSA (ratio 10:3) for 16 h ON day 2-3. The cells were washed to remove palmitate-BSA, and then incubated with 10 uM sulforaphane (SFN) for 28 h. The cells were washed 3 times with glucose output medium (GOM) without glucogenic substrates (118 mM NaCl, 4.7 mM KCl, 1.2 mM MgSO4, 1.2 mM KH2P04, 1.2 mM CaC12, 20 mM NaHCO3, 25 mM HEPES pH 7.4 and 0.025% BSA). Then 500 ul of GOM (118 mM NaCl, 4.7 mM KCl, 1.2 mM MgSO4, 1.2 mM KH2PO4, 1.2 mM CaCl2, 20 mM NaCO3, 25 mM HEPES pH 7.4, 0.025% BSA, 20 mM lactate, 2 mM pyruvate and 10 mM glutamine) and GOM with the addition of 10 or 100 nM insulin was added, and the cells were allowed to incubate for 5 h. After that, most of the incubation medium (375 ul) was removed and used for glucose measurements. The cells were washed once with cold PBS and lyzed with 200 ul RIPA buffer for determination of protein concentration. To ensure that the buffer samples were free of cells they were centrifuged for 5 min at 0.2 g and the supernatant transferred to a new tube. The cell lysates were likewise centrifuged for 5 min at 10,000 g and 4° C. and the supernatant transferred to a new tube. Glucose concentration in the buffer samples was determined using the AmplexRed Glucose/Glucose Oxidase Assay Kit (LifeTechnologies no. A22189) following the manufacturer's instructions. Protein concentration in the cell lysates was measured using Pierce BCA Protein Assay Kit (ThermoScientific no. 23225).

Figure 3:
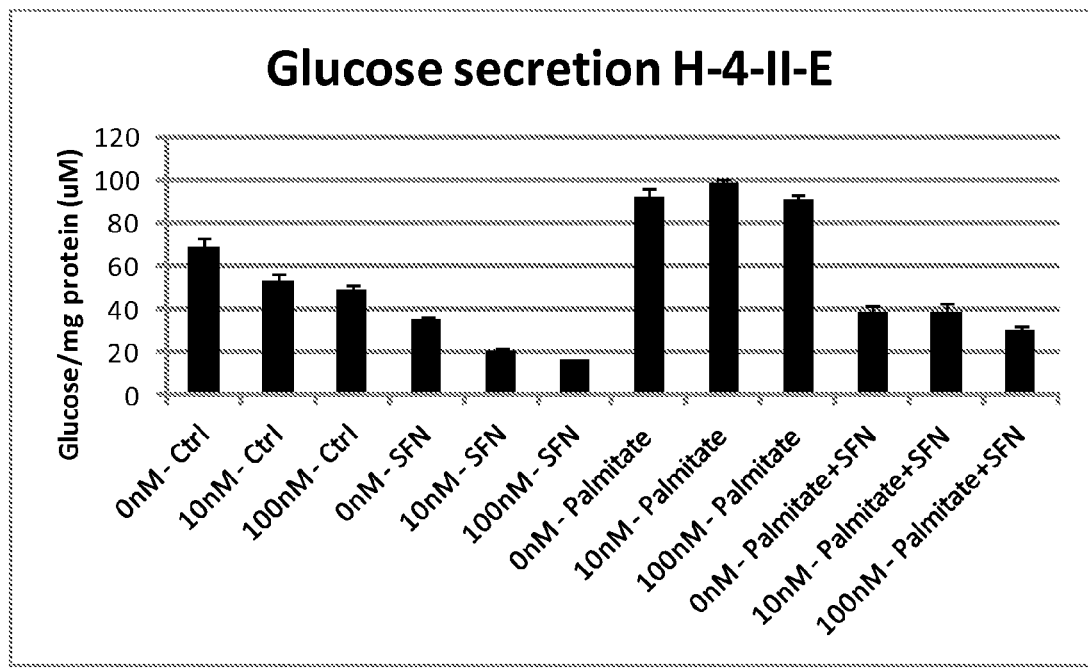
FIG. 3 displays hepatic glucose secretion of insulin-sensitive (the first 6 bars) and insulin-resistant (induced by palmitate) liver cells, untreated (Ctrl) or incubated for 24 h with sulforaphane (SFN).

FIG. 3 shows that the sulforaphane incubation decreases hepatic glucose output both in insulin-sensitive (the first 6 bars) and insulin-resistant (induced by palmitate) liver cells. This clearly shows that the sulforaphane treatment improves the hepatic insulin sensitivity.

CONCLUSIONS

In summary, the herein above provided examples clearly show that sulforaphane treatment specifically reduces insulin resistance in the liver tissue of a subject.

The invention claimed is:

1. A method of treating or reducing insulin resistance of the liver and/or improving hepatic insulin sensitivity wherein, the mammal to be treated, has an insulin resistance index of the liver that is higher than the insulin resistance index of other metabolic tissue, the method comprising the step of administering an effective amount of sulforaphane, or a plant extract comprising an effective amount of sulforaphane, to a mammal in need thereof.

2. The method according to claim 1, wherein said method improves glucose tolerance.

3. The method according to claim 1, wherein sulforaphane, or the plant extract comprising sulforaphane, is administrated by injection or orally.

4. The method according to claim 1, wherein the effective amount of sulforaphane comprises a daily administered dose of sulforaphane ranging from 10 to 1000 µmole.

5. The method according to claim 1, wherein the effective amount of sulforaphane administered to said mammal is a daily administered dose ranging from 1 to 100 mg/kg of the mammal's body weight.

6. The method according to claim 1, wherein, in the mammal to be treated, the insulin resistance of metabolic tissue other than the liver is not increased.

7. The method according to claim 1, wherein, in the mammal to be treated, the insulin sensitivity of metabolic tissue other than the liver is not decreased.

8. The method according to claim 1, wherein said plant extract is obtained from broccoli sprouts, Brussels sprouts, cabbage, cauliflower, bok choy, kale, collards, Chinese broccoli, broccoli raab, kohlrabi, mustard, turnip, radish, arugula, or watercress.

9. The method according to claim 4, wherein the daily administered dose of sulforaphane is 50 to 500 µmole.

10. The method according to claim 9, wherein the daily administered dose of sulforaphane is 100 to 200 µmole.

11. The method according to claim 5, wherein the daily administered dose of sulforaphane to said mammal to be treated is from 1 to 100 mg/kg of the mammal's body weight.

12. The method according to claim 11, wherein the daily administered dose of sulforaphane to said mammal to be treated is from 5 to 50 mg/kg of the mammal's body weight.

13. A method of treating or reducing insulin resistance of the liver and/or improving hepatic insulin sensitivity in a mammal in need thereof, the method comprising administering to said mammal, an effective dose of sulforaphane, or a plant extract comprising an effective amount of sulforaphane, wherein prior to administration of the effective dose, the mammal has an insulin resistance index that is higher in the liver than in other metabolic tissue and wherein the other metabolic tissue comprises body fat or muscles.

14. The method according to claim 13, wherein the effective dose comprises a daily administered dose of sulforaphane ranging from 10 to 1000 µmole.

* * * * *